(12) United States Patent
Zoba

(10) Patent No.: US 11,913,258 B2
(45) Date of Patent: Feb. 27, 2024

(54) DEVICE WITH RECEIVING CHAMBER AND TRIGGER MECHANISM FOR SECURELY CONSTRAINING AN OBJECT

(71) Applicant: Benjamin Robert Zoba, Beverly, MA (US)

(72) Inventor: Benjamin Robert Zoba, Beverly, MA (US)

(*) Notice: Subject to any disclaimer, the term of this patent is extended or adjusted under 35 U.S.C. 154(b) by 510 days.

(21) Appl. No.: 17/179,017

(22) Filed: Feb. 18, 2021

(65) Prior Publication Data
US 2022/0259895 A1    Aug. 18, 2022

(51) Int. Cl.
*E05B 75/00*    (2006.01)
*E05B 73/00*    (2006.01)

(52) U.S. Cl.
CPC .............. *E05B 75/00* (2013.01); *E05B 73/00* (2013.01)

(58) Field of Classification Search
CPC ................................. E05B 73/00; E05B 75/00
See application file for complete search history.

(56) References Cited

U.S. PATENT DOCUMENTS

| | | | | |
|---|---|---|---|---|
| 980,651 A * | 1/1911 | Malcolm | ................. | E05B 75/00 70/17 |
| 1,112,867 A * | 10/1914 | Taylor et al. | ........ | A01K 15/003 119/806 |
| 1,147,423 A * | 7/1915 | Murphy | ................... | E05B 75/00 70/17 |
| 1,199,100 A * | 9/1916 | Murphy | ................... | E05B 75/00 70/17 |
| 5,460,373 A * | 10/1995 | McNutt | ................... | A01K 97/14 119/807 |
| 5,482,271 A * | 1/1996 | McNutt | ................... | A01K 97/14 119/808 |
| 5,555,751 A * | 9/1996 | Strickland | ............... | E05B 75/00 70/16 |
| 8,307,676 B2 * | 11/2012 | Irisawa | ................... | F41B 15/02 70/17 |
| 2007/0000451 A1 * | 1/2007 | Goto | ....................... | E05B 75/00 119/802 |

* cited by examiner

*Primary Examiner* — Christopher J Boswell
(74) *Attorney, Agent, or Firm* — Jonathon P. Western (57) ABSTRACT

An apparatus can include: a housing configured to form a receiving chamber that is operable to receive an object; first and second paddles disposed at a distal end of the receiving chamber; a constraining bar movably disposed within the housing and configured to translate linearly along a length of the receiving chamber; and a trigger mechanism configured to releasably couple the constraining bar to the housing. When the constraining bar is in a loaded position, the trigger mechanism can be configured to release the constraining bar in response to a proximally-directed force exerted on the constraining bar, causing the constraining bar to translate distally along the length of the receiving chamber.

20 Claims, 8 Drawing Sheets

DEVICE WITH RECEIVING CHAMBER AND TRIGGER MECHANISM FOR SECURELY CONSTRAINING AN OBJECT

TECHNICAL FIELD

The present disclosure relates generally to devices for securely constraining an object and, more particularly, to devices with a receiving chamber and a trigger mechanism for performing the same.

BACKGROUND

Generally, in situations of lawlessness, such as riots, civil disturbances, or other criminal activity, the risk of injury to both humans and property can be high. Security forces (e.g., police, military, etc.) are often tasked with taking measures to prevent or mitigate such injury by controlling, dispersing, or arresting individuals involved. To this end, the security forces frequently are equipped with a variety of devices designed to assist in the restraint or incapacitation of offenders. Conventional examples of these devices include handcuffs, tear gas, rubber bullets, and electric tasers.

However, in a situation where restraining a single individual non-lethally is imperative, such devices suffer from myriad shortcomings. For example, the devices can be difficult to apply on a fast-moving target (e.g., handcuffs), unnecessarily excessive in scope (e.g., tear gas), or risk inflicting too severe an injury (e.g., rubber bullets and electric tasers). Accordingly, there is a need for a device capable of being wielded to efficiently, accurately, and securely constrain a moving target. Moreover, it is necessary that the device be capable of deployment in a non-lethal manner.

SUMMARY

The present disclosure provides a device for securely constraining an object, such as a person, or more particularly, a person's limb, a rod, a post, or the like. The device can include a housing that forms a receiving chamber in which the object is received. Rotating paddles can be disposed at a distal end of the receiving chamber, opposite a base portion of the housing. A constraining bar can be disposed within the housing so as to move linearly along the length of the receiving chamber, and a trigger mechanism can initiate, or trigger, movement of the constraining bar in the direction of the paddles. Because movement of the constraining bar in the opposite direction can be precluded, an object inside of the receiving chamber can be trapped therein between the constraining bar, the paddles, and the housing, thereby constraining the object securely. If the object being constrained is a potential criminal offender, law enforcement can then be deployed to perform a safe arrest.

In accordance with embodiments of the present disclosure, an apparatus can include: a housing configured to form a receiving chamber that is operable to receive an object, the housing having a base portion disposed at a proximal end of the housing and first and second housing arms extending outwardly from the base portion to form an opening at a distal end of the housing, the first and second housing arms disposed at opposite sides of the receiving chamber, respectively; first and second paddles disposed at a distal end of the receiving chamber, the first and second paddles rotatably coupled to respective distal ends of the first and second housing arms and extending inwardly therefrom; a constraining bar movably disposed within the housing and configured to translate linearly along a length of the receiving chamber, the constraining bar configured to move between a loaded position in which the constraining bar is positioned at a proximal end of the receiving chamber under tension and a released position in which the constraining bar is released from tension and positioned distal of the proximal end of the receiving chamber; and a trigger mechanism configured to releasably couple the constraining bar to the base portion. When the constraining bar is in the loaded position, the trigger mechanism can be configured to release the constraining bar in response to a proximally-directed force exerted on the constraining bar, causing the constraining bar to translate distally along the length of the receiving chamber.

The trigger mechanism can be configured to couple the constraining bar to the base portion when the constraining bar is in the loaded position and to de-couple the constraining bar from the base portion when the constraining bar is in the released position.

The trigger mechanism can include a holding device rotatably disposed on the base portion, the holding device configured to rotate between a holding position in which the holding device attaches to the constraining bar when the constraining bar is in the loaded position, such that the constraining bar is prevented from translating distally along the length of the receiving chamber, and a retracted position in which the holding device detaches from the constraining bar when the constraining bar is in the released position, such that the constraining bar is enabled to translate distally along the length of the receiving chamber.

The holding device can be configured to extend in a direction parallel to the length of the receiving chamber when the holding device is in the holding position and to extend in a direction non-parallel to the length of the receiving chamber when the holding device is in the retracted position.

The trigger mechanism can further include a holding device elastic member connected at a first end thereof to the base portion and at a second end thereof to the holding device, the holding device elastic member configured to transition between a resting state when the holding device is in the retracted position and a tensioned state when the holding device is in the holding state, causing extension of the holding device elastic member.

The trigger mechanism can further include one or more constraining bar elastic members connected at a first end thereof to the constraining bar and at a second end thereof to a distal portion of the housing, the one or more constraining bar elastic members configured to transition between a resting state when the constraining bar is in the released position and a tensioned state when the constraining bar is in the loaded position, causing extension of the one or more constraining bar elastic members.

When the holding device is in the holding position, causing the one or more constraining bar elastic members to be in the tensioned state, the holding device and the one or more constraining bar elastic members can be configured to exert opposing forces on the constraining bar, such that the constraining bar is held in the loaded position under tension.

In response to the proximally-directed force exerted on the constraining bar when the constraining bar is in the loaded position, causing temporary proximal translation of the constraining bar, the holding device elastic member can be configured to pull the holding device toward the retracted position, such that the constraining bar is released from tension, and the one or more constraining bar elastic members are configured to pull the constraining bar toward the distal end of the receiving chamber, such that the constraining bar translates distally along the length of the receiving chamber.

The first and second paddles can be rotatably coupled to the respective distal ends of the first and second housing arm via first and second axle members mounted to the housing, such that the first and second paddles are configured to rotate about the first and second axle members, respectively.

The first and second paddles can be configured to rotate between a neutral position in which the first and second paddles are held at rest and an inwardly rotated position in which the first and second paddles rotate inwardly with respect to the receiving chamber from the neutral position.

When the first and second paddles are in the neutral position, the first and second paddles can extend inwardly from the respective distal ends of the first and second housing arms at an angle substantially perpendicular to the first and second housing arms.

The apparatus can further include first and second paddle elastic members connected at a first end thereof to the first and second paddles, respectively, and at a second end thereof to the housing, the first and second paddle elastic members configured to transition between a resting state when the first and second paddles are in the neutral position and a tensioned state when the first and second paddles are in the inwardly rotated position, causing extension of the first and second paddle elastic members.

When the first and second paddles are in the inwardly rotated position, the first and second paddle elastic members can be configured to pull the first and second paddles, respectively, in a direction causing the first and second paddles to rotate outwardly with respect to the receiving chamber toward the neutral position.

The apparatus can further include first and second constraining cords connected at a first end thereof to the first and second paddles, respectively, and at a second end thereof to the base portion, the first and second constraining cords configured to prevent the first and second paddles from rotating outwardly with respect to the receiving chamber from the neutral position.

The apparatus can further include a locking mechanism coupled to the housing and the constraining bar.

The locking mechanism can be configured to prevent the constraining bar from translating proximally along the length of the receiving chamber when the constraining bar is in the released position.

The locking mechanism can include first and second locking ties extending at least partially along the length of the receiving chamber and coupled to the housing and the constraining bar, the first and second locking ties configured to enable the constraining bar to translate distally along the length of the receiving chamber while preventing the constraining bar from translating proximally along the length of the receiving chamber.

The first and second locking ties can be coupled to the housing at a plurality of locations, including a distal location of the housing and a proximal location of the housing, and movably coupled to the constraining bar at a location between the distal location of the housing and the proximal location of the housing.

The housing can include first and second housing plates connected to each other via a plurality of connecting rods extending in a direction perpendicular to the length of the receiving chamber, forming a gap between the first and second housing plate.

At least a portion of the constraining bar can be disposed in the gap between the first and second housing plates, and at least a portion of the first and second paddles can be disposed in the gap between the first and second housing plates.

The apparatus can further include a projecting shaft coupled to the base portion and extending outwardly therefrom. The projecting shaft can include: an inner shaft attached to the housing; a hollow outer shaft with a spring disposed therein, the outer shaft configured to receive the inner shaft; and an adjustable locking latch disposed on a surface of the outer shaft, the locking latch configured to transition between a locked position in which the locking latch contacts the inner shaft so as to lock together the inner shaft and the outer shaft and an unlocked position in which the locking latch is removed from the inner shaft so as to enable the inner shaft to move independently of the outer shaft. When the outer shaft receives the inner shaft, such that a surface of the inner shaft that is disposed inside of the outer shaft compresses the spring, the spring can be configured to decompress when the locking latch is transitioned from the locked position to the unlocked position, causing longitudinal movement of the inner shaft independent of the outer shaft.

BRIEF DESCRIPTION OF THE DRAWINGS

The embodiments herein may be better understood by referring to the following description in conjunction with the accompanying drawings in which like reference numerals indicate identically or functionally similar elements, of which.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION OF THE EMBODIMENTS

Hereinafter, embodiments of the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be further understood that the term "coupled" (or "connected," "attached," or the like), when used in this specification, encompasses both direct couplings (e.g., two objects in direct contact with each other) and indirect couplings (e.g., two objects not in direct contact with each other but indirectly coupled via an intermediate object), unless explicitly stated otherwise. As used herein, the term "and/or" includes any and all combinations of one or more of the associated listed items.

Referring now to embodiments of the present disclosure, the constraining device discussed herein can be wielded by a user to efficiently and securely constrain a target, such as a person, or more specifically, a person's limb (e.g., leg, arm, etc.), a post, a rod, or so on, in a non-lethal manner. The constraining device can be employed in a wide variety of environments. For example, law enforcement (e.g., police, military, etc.) can utilize the constraining device to non-lethally restrain a suspect amidst criminal activity, a riot, or other disturbances. As another example, non-law enforcement citizens can utilize the constraining device to non-lethally restrain a suspect temporarily to allow time for police to arrive and make an arrest. As yet another example, multiple persons can be equipped with the constraining devices in a game-like scenario (e.g., capture the flag), wherein players use the device to attempt to restrain their opponents within the context of applicable game rules. It is to be understood that the applicability of the constraining device described herein is not limited to any one environment or scenario.

Figure 1A:
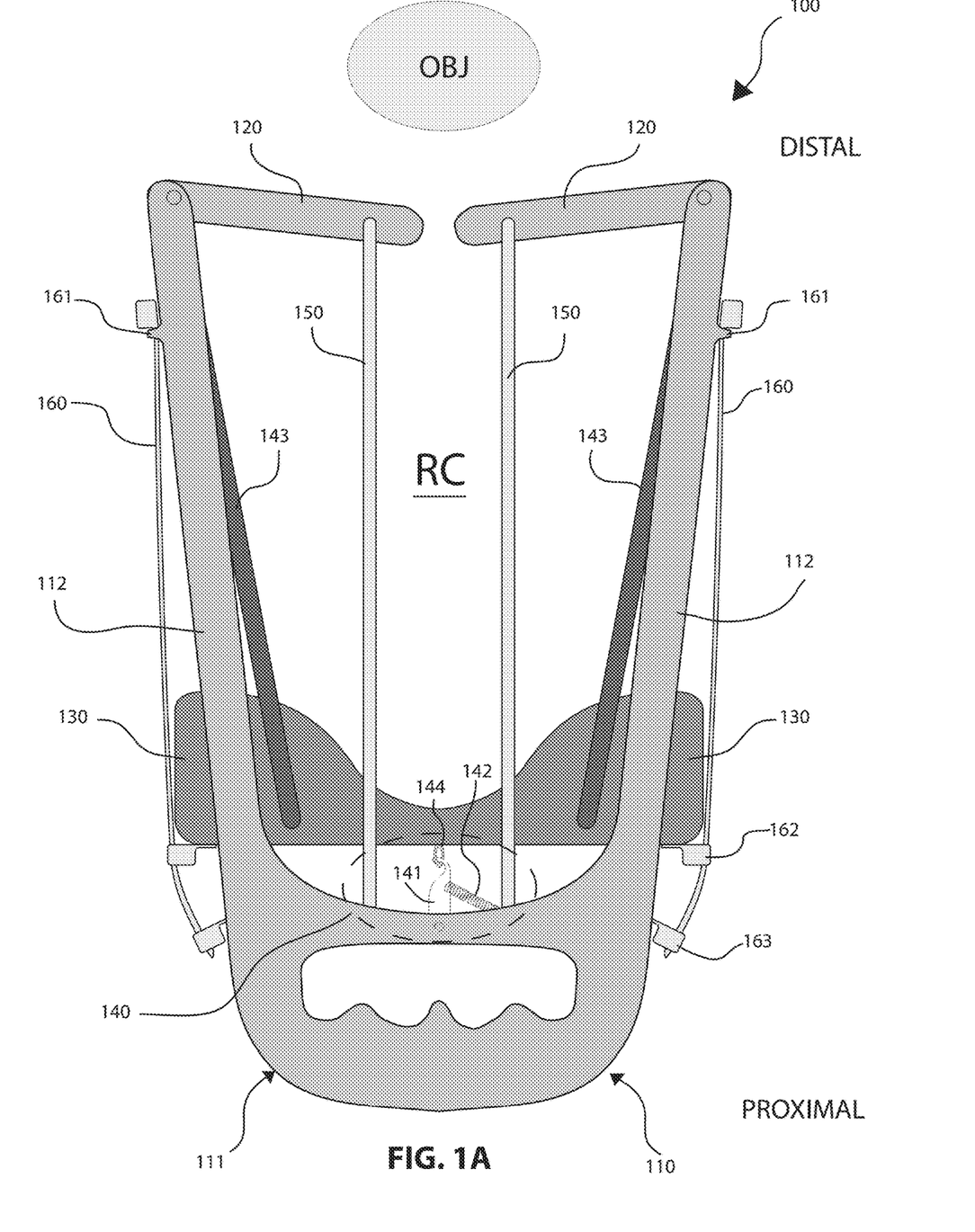
FIGS. 1A-1C are a front view, a side view, and a top view, respectively, of a constraining device.
Figure 1B:
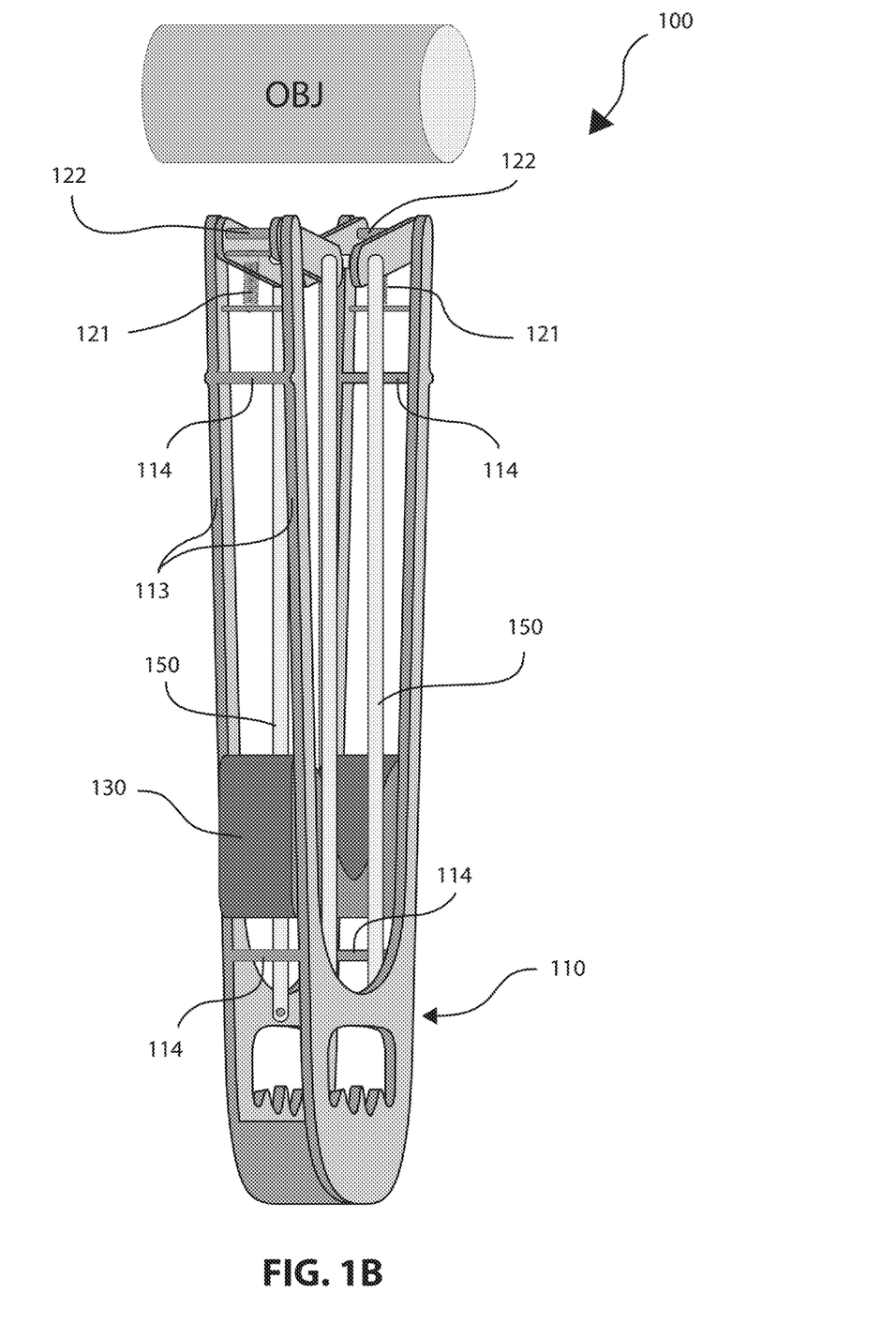
Figure 1C:
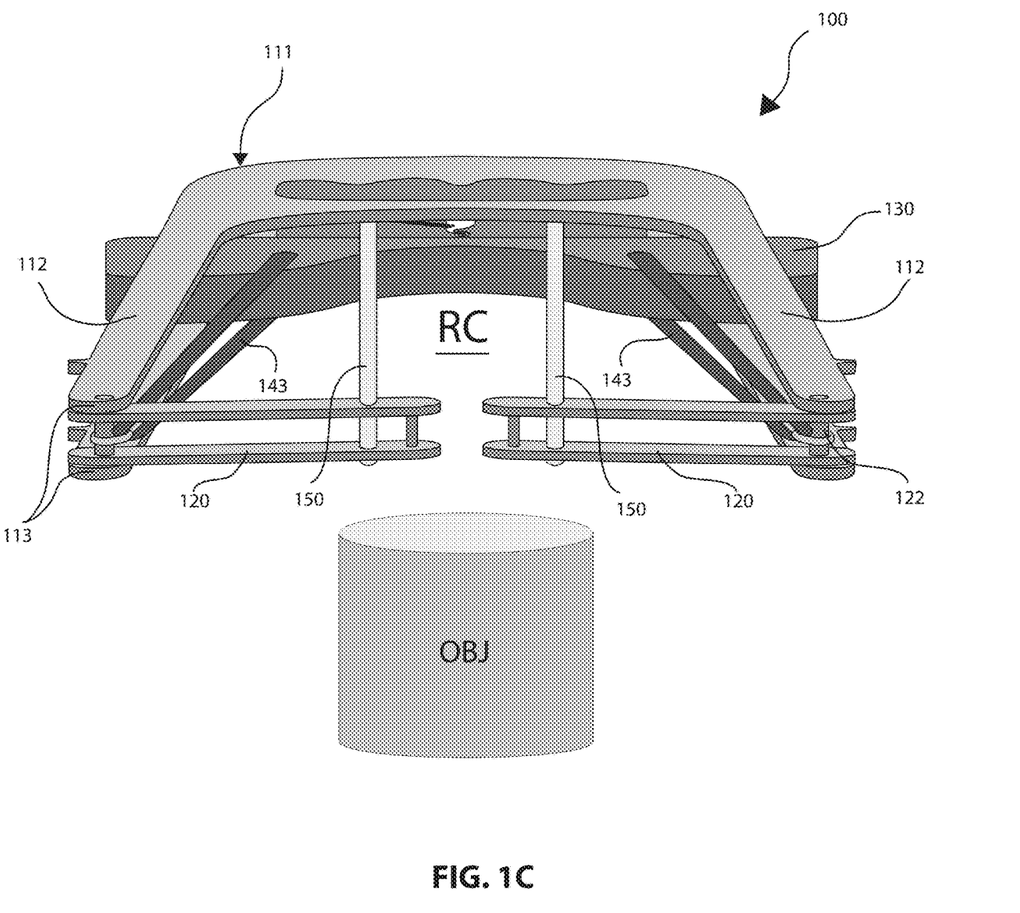

Firstly, FIGS. 1A-1C illustrate a front view, a side view, and a top view, respectively, of a constraining device 100. It is noted that FIG. 1B illustrates a side view of the constraining device 100 that is offset from a direct side view, resulting in a three-dimensional side view of the constraining device 100. Similarly, FIG. 1C illustrates a top view of the constraining device 100 that is offset from a direct top view, resulting in a three-dimensional top view of the constraining device 100. It is further noted that particular elements of the constraining device 100, including the trigger mechanism 140, the locking mechanism 160, and sub-components thereof, are omitted from the view of FIG. 1B to enhance the viewing of the remaining elements.

As shown in FIGS. 1A-1C, the constraining device 100 can include a housing 110 which forms the base of the device 100. The housing 110 can be configured to form a receiving chamber RC that is operable to receive an object OBJ. The housing 110 can be formed of various substantially rigid materials including, but not limited to, metals (e.g., steel), plastics, ceramics, wood, hardened rubbers, or any combination thereof. The receiving chamber RC can represent an area inside of the housing 110, and its various parts (described below), capable of receiving the object OBJ. For example, the receiving chamber RC can represent an interior area defined by the base portion 111, the housing arms 112, and the first and second paddles 120. The object OBJ can represent any object capable of being received in the receiving chamber RC including, but not limited to, a person, or more specifically, a person's limb (e.g., leg, arm, etc.), a post, a rod, and so on.

The housing 110 can be formed in various shapes and sizes and is not limited to any particular dimensions. For example, the housing 110 can be formed to adopt a fork- or U-shape within which the receiving chamber RC is defined. In some embodiments, the housing 110 can be formed of multiple layers, for example, first and second housing plates 113, connected to each other via a plurality of connecting rods 114 (see FIGS. 1B and 1C). The housing plates 113 can be symmetrically formed and connected to each other to improve the structural rigidity and durability of the housing 110. The connecting rods 114 can extend in a direction perpendicular to the length of the receiving chamber RC, and perpendicular to a plane of the housing plates 113. Furthermore, the connecting rods 114 can be disposed at various locations of the housing 110, such as a distal location of the housing 110 and a proximal location of the housing, as shown in FIG. 1B. The connecting rods 114 can also be disposed at right and left sides of the housing 110, where applicable, as further shown in FIG. 1B.

Because the first and second housing plates 113 can be separated via perpendicularly extending connecting rods 114, a gap can be formed between the housing plates 113, providing a degree of depth to the constraining device 100. Portions of other components of the constraining device 100, such as the first and second paddles 120 and the constraining bar 130, can be disposed in the gap between the housing plates 113. Such components can move and/or rotate within the gap. Furthermore, the gap between the first and second housing plates 113 formed by the connecting rods 114 extending therebetween can have various lengths, and is not limited to any one particular length. For example, in some embodiments, the gap between the housing plates 113 can be within the range of 0.25 inches to 2.0 inches. The gap between the housing plates 113 can be uniform throughout the housing 110, or can be greater in a certain region of the housing 110 than another region thereof. In other embodiments, the housing 110 can be formed without multiple plates, but rather a singular, unified body without the aforementioned gap.

Referring again to FIGS. 1A-1C, the housing 110 can include a base portion 111 disposed at a proximal end of the housing 110. In some embodiments, a user of the constraining device 100 can hold onto the device 100 by the base portion 111. For example, the base portion 111 can include a grip portion as shown throughout the figures. The grip portion can include a cut-out portion formed in the base portion 111 in some cases. The grip portion can further include indentations formed to fit the fingers of a user to enhance the user's grip of the device 100. If the housing 110 is formed with multiple layers, e.g., first and second housing plates 113, in the manner described above, the base portion 111 can likewise include the multiple layers at the location of the base portion 111, and can include one or more connecting rods 114 connecting the multiple layers.

The housing 110 can further include first and second housing arms 112 extending outwardly from the base portion 111 to form an opening at a distal end of the housing 110. The first and second housing arms 112 can be disposed at opposite sides of the receiving chamber, respectively, and therefore define lateral (e.g., side) boundaries of the receiving chamber RC. If the housing 110 is formed with multiple layers, e.g., first and second housing plates 113, in the manner described above, each of the housing arms 112 can likewise include the multiple layers at the location of the particular housing arm 112, and can include one or more connecting rods 114 connecting the multiple layers.

The constraining device 100 can further include first and second paddles 120 disposed at a distal end of the receiving chamber RC. The first and second paddles 120 can be rotatably coupled to respective distal ends of the first and second housing arms 112 and extend inwardly therefrom.

The first and second paddles 120 can define the distal boundary of the receiving chamber RC.

Figure 2A:
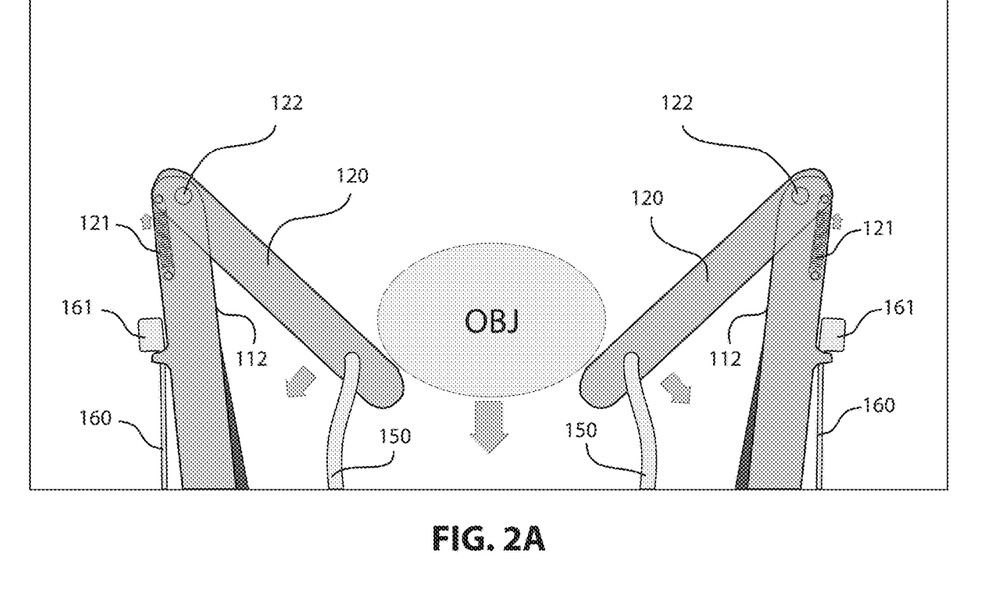
FIGS. 2A and 2B include operational views of rotating paddles of the constraining device of FIGS. 1A-1C.
Figure 2B:
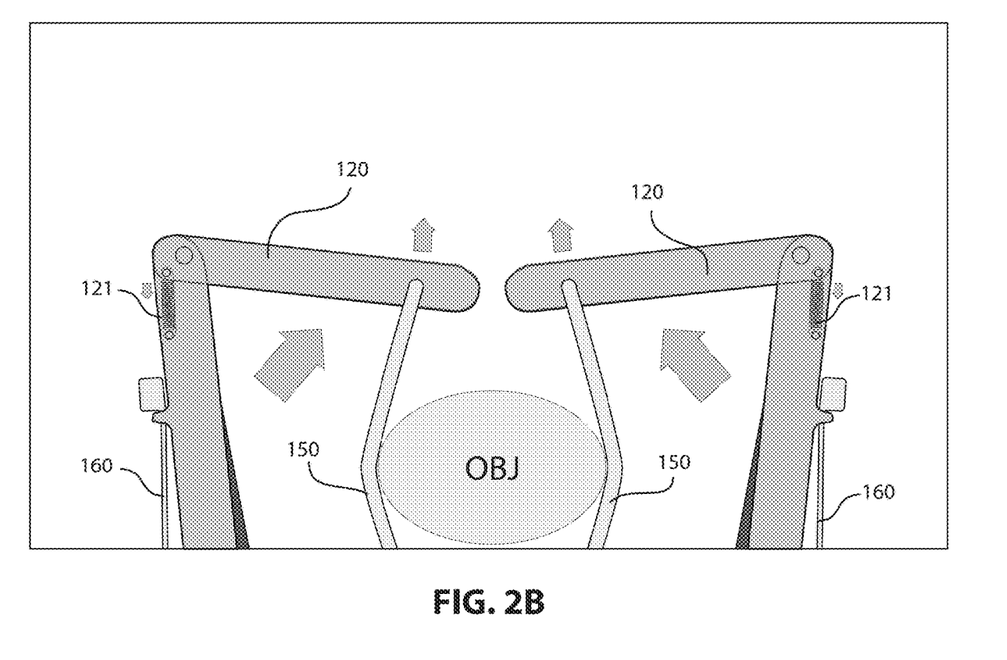

Referring to FIGS. 2A and 2B, which illustrate operational views of the first and second paddles 120 of the constraining device 100, the first and second paddles 120 can be affixed to the distal ends of the first and second housing arms 112 via first and second axle members, respectively, mounted to the housing 110. The axle members 122 can be circular such that the first and second paddles 120 are able to rotate about the first and second axle members 120, respectively. It is noted that particular elements of the constraining device 100, including the axle members 122 and paddle elastic members 121, are made visible in FIGS. 2A and 2B for the purpose of enhancing the viewing of the said elements, although such elements in practice may not be visible from the illustrated angle, as would be understood by a person of ordinary skill in the art.

In operation, the first and second paddles 120 can rotate between a "neutral position" (e.g., see FIG. 1A), in which the first and second paddles 120 are held at rest, and an "inwardly rotated position" (e.g., see FIG. 2A) in which the first and second paddles 120 rotate inwardly with respect to the receiving chamber RC from the neutral position. According to some embodiments, the neutral position can refer to a position in which the first and second paddles 120 extend inwardly from the respective distal ends of the first and second housing arms 112 at an angle substantially perpendicular to the first and second housing arms 112. According to other embodiments, the neutral position can refer to a position in which the first and second paddles 120 extend inwardly from the respective distal ends of the first and second housing arms 112 at an angle less than perpendicular to the first and second housing arms 112. However, the angle of the first and second paddles 120 with respect to the first and second housing arms 112, respectively, while in the neutral position is not limited solely to any particular angle.

In detail, the first and second paddles 120 can be "spring-loaded" such that the paddles 120 tend to return to the neutral position upon rotation, caused by the object OBJ entering the receiving chamber RC, for example. To this end, the constraining device 100 can include first and second paddle elastic members 121 connected at a first end thereof to the first and second paddles 120, respectively, and at a second end thereof to the housing 110. The first and second paddle elastic members 121 can be disposed outside of the axle members 122, with respect to the receiving chamber RC. The first and second paddle elastic members 121 can include any material having elastic structural properties such as, for example, coil springs, rubber, elastic fibers, and so on. For the purpose of demonstration, but without limitation, the first and second paddle elastic members 121 are illustrated in the figures as coil springs.

In operation, the first and second paddle elastic members 121 can transition between a "resting state" when the first and second paddles 120 are in the neutral position (e.g., see FIG. 1A) and a "tensioned state" (e.g., see FIG. 2A) when the first and second paddles 120 are in the inwardly rotated position. When in the tensioned state, the first and second paddles 120 can cause extension of the first and second paddle elastic members 121 beyond their natural, resting state, thus storing potential energy. As a result, when the first and second paddles 120 are in the inwardly rotated position, the first and second paddle elastic members 121 can exert a force on the first and second paddles 120, respectively, thus pulling the paddles 120 in a direction causing the first and second paddles 120 to rotate outwardly with respect to the receiving chamber RC toward the neutral position (e.g., see FIG. 2B). Therefore, once an object OBJ has passed through the first and second paddles 120 into the receiving chamber RC, the first and second paddle elastic members 121 can pull the paddles 120 out of the receiving chamber RC.

As the first and second paddles 120 rotate out of the receiving chamber RC toward the neutral position, as shown in FIG. 2B, various mechanisms can be employed to prevent the paddles 120 from rotating outwardly beyond the neutral position. As such, the first and second paddles 120 can function as a one-way door allowing the object OBJ to enter into the receiving chamber RC, through the paddles 120, without being able to escape therethrough. For example, the constraining device 120 can include first and second constraining cords 150 connected at a first end thereof to the first and second paddles 120, respectively, and at a second end thereof to the base portion 111. The length of the first and second constraining cords 150 can be controlled such that first and second paddles 120 are in the desired neutral position when the constraining cords 150 are fully extended (i.e., non-deformed), as shown in FIG. 1A, for example. In addition to preventing the first and second paddles 120 from rotating outwardly with respect to the receiving chamber RC from the neutral position, the first and second constraining cords 150 can also restrict the lateral movement of the object OBJ within the receiving chamber RC, as shown in FIG. 2B, so as to maintain the object OBJ within the center of the receiving chamber RC.

Alternatively, the constraining device 100 can include a connecting rod or bolt (not shown) positioned outside of the first and second axle members 122. Once the first and second paddles 120 reach the neutral position, the connecting rod or bolt can be positioned to block a respective portion of the first and second paddles 120 that protrudes past the axle members 122 (on the exterior side of the housing 110), thus preventing outward rotation of the paddles 120 beyond the neutral position.

Referring again to FIGS. 1A-1C, the constraining device 100 can further include a constraining bar 130 movably disposed within the housing 110. If the housing 110 is formed with formed first and second housing plates 113, as described above, the constraining bar 130 can be disposed in the gap formed therebetween. The constraining bar 130 can be configured to translate linearly along a length of the receiving chamber RC (i.e., from the proximal end of the receiving chamber RC to the distal end of the receiving chamber RC, and vice versa). The constraining bar 130 can extend transversely across the width of the receiving chamber RC. In some embodiments, the constraining bar 130 can be rectangularly shaped with a cutout portion formed in the distal side thereof to accommodate the shape of the object OBJ, although the shape of the constraining bar 130 is not limited solely thereto.

In operation, the constraining bar 130 can be disposed within the housing 110 so as to move between a "loaded position" (e.g., see FIG. 1A), in which the constraining bar 130 is positioned at a proximal end of the receiving chamber RC under tension, and a "released position" (e.g., see FIG. 4, v. and vi.), in which the constraining bar 130 is released from tension and positioned distal of the proximal end of the receiving chamber RC. The movement of the constraining bar 130 can be controlled by a trigger mechanism 140 configured to releasably couple the constraining bar 130 to the housing, particularly the base portion 111. Specifically, the trigger mechanism 140 can couple the constraining bar 130 to the base portion 111 when the constraining bar 130 is in the loaded position and de-couple the constraining bar 130 from the base portion 111 when the constraining bar 130 is in the released position. Thus, when the constraining bar 130 is in the loaded position, the trigger mechanism 140 can release the constraining bar 130 in response to a proximally-directed force exerted on the constraining bar 130, causing the constraining bar 130 to translate distally along the length of the receiving chamber RC to the released position. The proximally-directed force exerted on the constraining bar 130 can be, for example, impact of the object OBJ upon a distal surface of the constraining bar 130.

The trigger mechanism 140 can include a holding device 141, a holding device elastic member 142, one or more constraining bar elastic members 143, and a holding device receiving member 144. The holding device 141 can be, for example, a tab, a rod, a shaft, etc. with a hook-like portion disposed at the end thereof. The holding device 141 can be rotatably mounted to the base portion 111 (e.g., via an axle, a pin, a rod, etc.) at a first end thereof, and formed at a second, opposite end thereof with the hook-like portion configured to latch onto the holding device receiving member 144. The holding device receiving member 144 can be disposed on a proximal side of the constraining bar 130 and can include, for example, an eyelet or a cut-out portion configured to receive the hook-like portion of the holding device 141.

In operation, the holding device 141 can be configured to rotate between a "holding position" (e.g., see FIG. 1A) in which the holding device 141 attaches to the constraining bar 130 (via holding device receiving member 144) when the constraining bar 130 is in the loaded position, and a "retracted position" (e.g., see FIG. 4, v. and vi.) in which the holding device 141 detaches from the constraining bar 130 when the constraining bar 130 is in the released position. Thus, when the constraining bar 130 is in the loaded position, the holding device 141 can hold onto the constraining bar 130 such that the constraining bar 130 is prevented from translating distally along the length of the receiving chamber RC. Conversely, when the constraining bar 130 is in the released position, the holding device 130 can release or detach from the constraining bar 130 such that the constraining bar 130 is enabled to translate distally along the length of the receiving chamber RC. In some embodiments, the holding device 141 can extend in a direction parallel to the length (i.e., longitudinal axis) of the receiving chamber RC when the holding device 141 is in the holding position, and extend in a direction non-parallel to the length of the receiving chamber RC when the holding device 141 is in the retracted position.

The holding device elastic member 142 can be connected at a first end thereof to the housing 110, particularly the base portion 111, and at a second end thereof to the holding device 141. The holding device elastic member 142 can include any material having elastic structural properties such as, for example, coil springs, rubber, elastic fibers, and so on. For the purpose of demonstration, but without limitation, the holding device elastic member 142 is illustrated in the figures as a coil spring. In operation, the holding device elastic member 142 can transition between a "resting state" (e.g., see FIG. 4, v. and vi.) when the holding device 141 is in the retracted position and a "tensioned state" (e.g., see FIG. 1A) when the holding device 141 is in the holding state. In the tensioned state, the position of the holding device 141 can cause extension of the holding device elastic member 142 beyond its natural, resting state, thus storing potential energy.

The one or more constraining bar elastic members 143 (e.g., elastic cords, rubber bands, coil springs, etc.) can be connected at a first end thereof to the constraining bar 130 and at a second end thereof to a distal portion of the housing 110. In some embodiments, the second end of the one or more constraining bar elastic members 143 can be connected to the first and second axle members 122. In operation, the one or more constraining bar elastic members 143 can transition between a "resting state" (e.g., see FIG. 4, vi.) when the constraining bar 130 is in the released position and a "tensioned state" when the constraining bar 130 is in the loaded position (e.g., see FIG. 4 i.). In the tensioned state, the position of the constraining bar 130 can cause extension of the one or more constraining bar elastic members 143 beyond its natural, resting state, thus storing potential energy. Furthermore, when the holding device 141 is in the holding position (e.g., see FIG. 4, i.), which can cause the one or more constraining bar elastic members 143 to be in the tensioned state, the holding device 141 and the one or more constraining bar elastic members 143 can exert opposing forces on the constraining bar 130 along the length of the receiving chamber RC. As a result, the constraining bar 130 can be held under tension in the loaded position. Alternatively, or additionally, the constraining bar 130 can be loaded with potential energy via one or more compression springs (not shown) connected to the proximal end of the housing 110.

Figure 3:
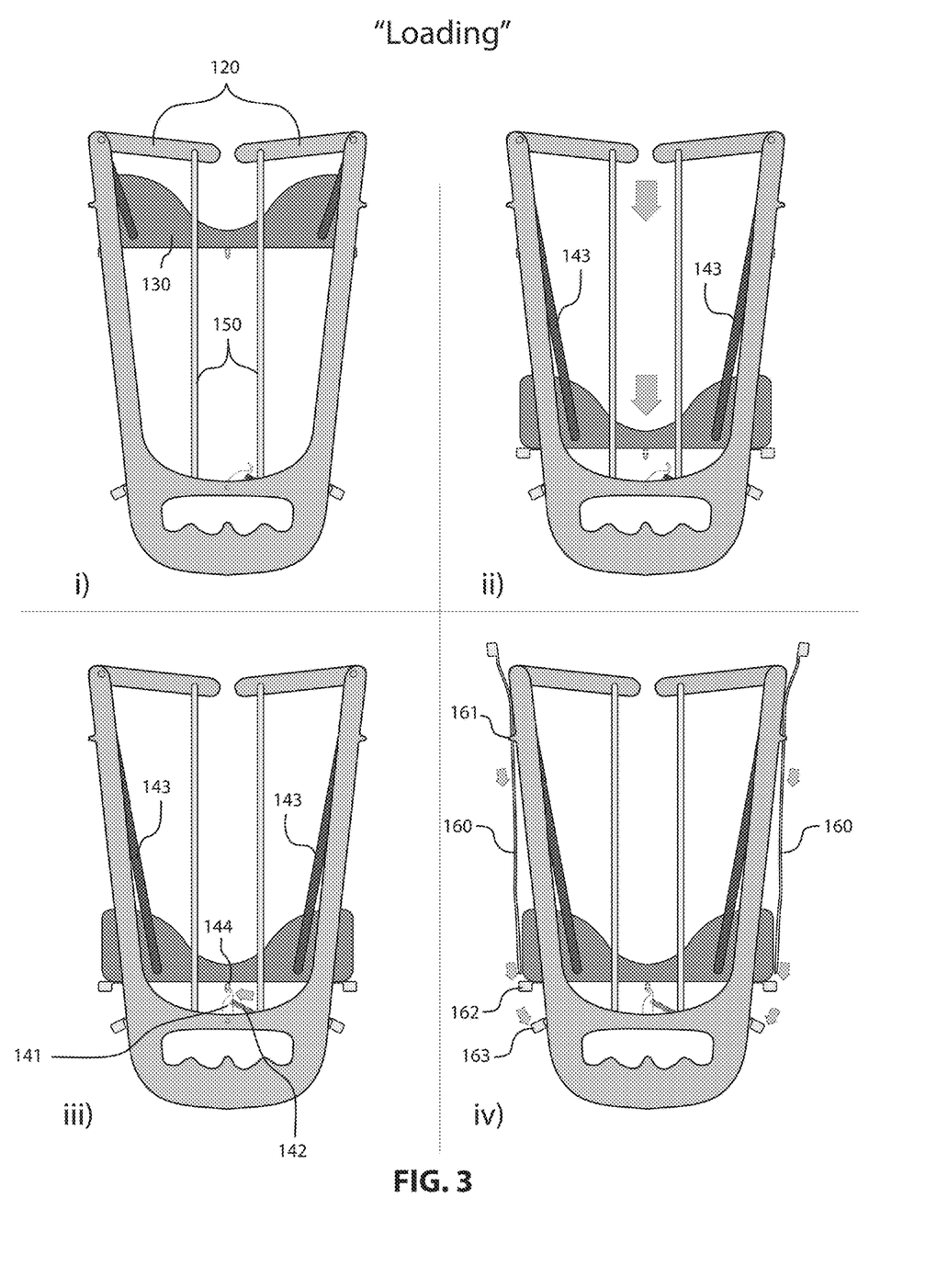
FIG. 3 includes operational views for loading the constraining device of FIGS. 1A-1C.

Referring next to FIG. 3, loading the constraining device 100 can involve pulling the constraining bar 130 proximally (i.e., away from the first and second paddles 120), thus stretching the one or more constraining bar elastic members 143 along the length of the receiving chamber RC (i.e., longitudinally), and setting the trigger mechanism 140 so as to hold or latch onto the constraining bar 130.

At FIG. 3, i., the constraining bar 130 can initially be positioned at a distal end of the receiving chamber RC. Here, the one or more constraining bar elastic members 143 can be in their resting (i.e., retracted) state.

At FIG. 3, ii., the constraining bar 130 can be pulled proximally along the length of the receiving chamber RC to a proximal end of the receiving chamber RC. The constraining bar 130 can be pulled in the proximal direction until the holding device receiving member 144 (e.g., eyelet, cut-out portion, etc.) disposed on the constraining bar 130 is within range of the holding device 141. Here, the one or more constraining bar elastic members 143 can be stretched along the length of the receiving chamber RC, transitioning the one or more constraining bar elastic members 143 into their tensioned (i.e., extended) state.

At FIG. 3, iii., the trigger mechanism 140 can couple the constraining bar 130 to the base portion 111. Specifically, the holding device 141 can rotate from the retracted position, in which the holding device 141 is detached from the constraining bar 130, to the holding position, in which the holding device 141 attaches to the constraining bar 130 (via holding device receiving member 144). The holding device elastic member 142, meanwhile, can transition from the resting state to the tensioned state, whereby the position of the holding device 141 causes extension of the holding device elastic member 142. Here, the constraining bar 130 can be in the loaded position, as the constraining bar 130 is under tension from the holding device 141 retaining the constraining bar 130 at a proximal end of the receiving chamber RC while the one or more constraining bar elastic members 143 exert a distally-directed force on the constraining bar 130, pulling the constraining bar 130 toward the first and second paddles 120.

At FIG. 3, iv., a locking mechanism can be added to the constraining device 100. The locking mechanism can couple to the housing 110 and the constraining bar 130 in order to prevent the constraining bar 130 from translating proximally along the length of the receiving chamber RC when the constraining bar 130 is released from the loaded position. Once the constraining bar 130 has been released and has constrained the object OBJ between the constraining bar 130 and the first and second paddles 120, the locking mechanism can affix the constraining bar in place, securely holding the object OBJ inside of the receiving chamber RC.

The locking mechanism can include first and second locking ties 160 extending at least partially along the length of the receiving chamber RC. The first and second locking ties 160 can include, for example, zip-ties or similar one-way locking mechanisms. In some embodiments, the first and second locking ties can extend along an outside of the first and second housing arms 112, respectively. The first and second locking ties 160 can be coupled to the housing 110 and the constraining bar 130. Once engaged, the first and second locking ties 160 can restrict the motion of the constraining bar 130 to only a single direction. Namely, the first and second locking ties 160 can enable the constraining bar 130 to translate distally along the length of the receiving chamber RC while preventing the constraining bar 130 from translating proximally along the length of the receiving chamber RC.

Furthermore, the first and second locking ties 160 can attach to the housing 110 at a plurality of locations. Such locations can include, for example, a distal location 161 of the housing 110 and a proximal location 163 of the housing 110. The first and second locking ties 160 can also be movably coupled to a location 162 disposed on the constraining bar 130. As such, the first and second locking ties 160 can move in conjunction with the constraining bar 130 as the constraining bar 130 moves distally along the length of the receiving chamber RC. The location 162 on the constraining bar can be located between the distal location 161 of the housing 110 and the proximal location 163 of the housing 110.

In operation, the first and second locking ties 160 can first be inserted through openings (not shown) formed in distal connecting rods 114 (location 161). Next, the first and second locking ties 160 can be inserted through respective female parts of two additional zip-ties affixed to the loaded constraining bar 130 (location 162). Lastly, the first and second locking ties 160 can be inserted into respective female parts of two additional zip-ties affixed to a proximal portion of the housing 110 (location 163). The affixed location 163 can hold the first and second locking ties 160 from moving as the affixed location 162 on the constraining bar 130 slides distally up the locking ties 160.

In this engaged position, the constraining bar 163 and its corresponding affixed location 162 can move distally along the first and second locking ties 160 toward the neutral, closed first and second paddles 120, but cannot move proximally away from the paddles 120 without disengaging (e.g., removing, cutting, etc.) the locking ties 160. Accordingly, the locking mechanism (i.e., first and second locking ties 160) can enable the constraining bar 130, upon release (i.e., retraction of the holding device 141), to move distally along the length of the receiving chamber RC (toward the first and second paddles 120), but not proximally, thus securing the object OBJ snugly inside of the receiving chamber RC between the constraining bar 130 and the first and second paddles 120.

Alternatively, the locking mechanism can include other one-way locking mechanisms, such as, for example, a pair of rods (not shown) with angled teeth disposed along the first and second housing arms 112, respectively. For instance, the rods can be fed through a spring-loaded angled tooth on each side of the constraining bar 130. Alternatively, one toothed rod (not shown) can be connected to the proximal side of the constraining bar 130 (e.g., at a central region thereof) extending proximally therefrom into a shaft (not shown) connected to a proximal portion of the housing 110. In such case, the toothed rod and the shaft as described above can function both as the locking mechanism and the trigger mechanism 140 using a spring-loaded hook or latch in a manner similar as described hereinabove. As, the toothed rod is fed through a spring-loaded angled tooth, the rod can be allowed to move distally but not proximally.

Figure 4:
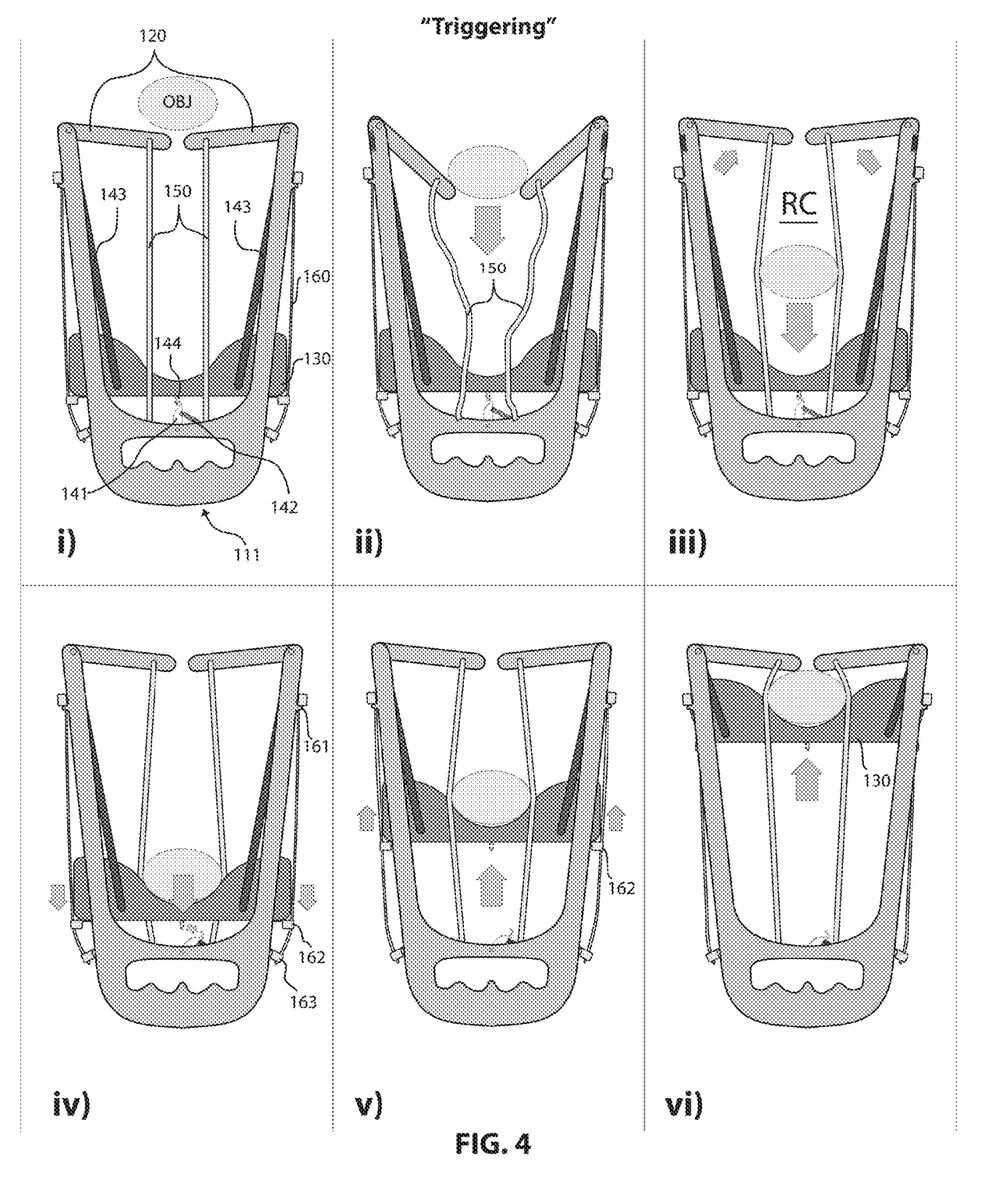
FIG. 4 includes operational views for triggering the constraining device of FIGS. 1A-1C.

Referring next to FIG. 4, triggering the constraining device 100 can involve release of the constraining bar 130 from the loaded position, causing the constraining bar 130 to accelerate distally toward the first and second paddles 120, and trapping the object OBJ inside of the receiving chamber RC between the distal surface of the constraining bar 130 and the proximal surface of the first and second paddles 120 (as well as the first and second constraining cords 150 on lateral sides of the object OBJ).

At FIG. 4, i., the trigger mechanism 140 can couple the constraining bar 130 to the base portion 111. Specifically, the holding device 141 can rotate to the holding position, in which the holding device 141 attaches to the constraining bar 130 (via holding device receiving member 144). The holding device elastic member 142 can transition to the tensioned state as a result, whereby the position of the holding device 141 causes extension of the holding device elastic member 142. Accordingly, the constraining bar 130 can be in the loaded position, as the constraining bar 130 is under tension from the holding device 141 retaining the constraining bar 130 at a proximal end of the receiving chamber RC while the one or more constraining bar elastic members 143 exert a distally-directed force on the constraining bar 130, pulling the constraining bar 130 toward the first and second paddles 120.

At FIG. 4, ii., the object OBJ can enter the receiving chamber RC via the first and second paddles 120. Contact between the object OBJ and the first and second paddles 120 can cause the paddles 120 to inwardly rotate (inwardly rotated position). In some embodiments, the object OBJ can travel proximally through the first and second paddles 120 and into the receiving chamber RC. In other embodiments, the object OBJ can remain substantially motionless while the constraining device 100 is thrusted upon the object OBJ, causing the object OBJ to enter the receiving chamber RC through the first and second paddles 120. In yet other embodiments, the object OBJ and the constraining device 100 can be in motion simultaneously in such a manner that the object OBJ enters the receiving chamber RC through the first and second paddles 120, as would be appreciated by a person of ordinary skill in the art. The inward rotation of the first and second paddles 120 can cause the first and second paddle elastic members 121 to extend (tensioned state), storing potential energy therein. Furthermore, the first and second constraining cords 150 may no longer be fully extended. The resultant slack in the first and second constraining cords 150 can cause them to deform, as exemplarily shown in FIG. 4, ii.

At FIG. 4, iii., as the object OBJ travels further proximally into the receiving chamber RC, the object OBJ can travel past the first and second paddles 120. Because the object OBJ is no longer in contact with the first and second paddles 120, the first and second paddle elastic members 121 can retract from their tensioned state, causing the first and second paddles 120 to rotate outwardly back to their neutral position in which the paddles 120 are held at rest. Here, the first and second paddles 120 can be prevented from rotating outwardly beyond their neutral position, as described in detail above, thus preventing the object OBJ from exiting the receiving chamber RC through the paddles 120.

At FIG. 4, iv., as the object OBJ continues to travel further into the receiving chamber RC, the proximally traveling object OBJ can strike the distal surface of the loaded constraining bar 130, resulting in a proximally-directed force exerted on the constraining bar 130. The contact pressure exerted on the constraining bar 130 by the object OBJ can push the constraining bar 130 in the proximal direction, causing temporary proximal translation of the constraining bar 130 toward the base portion 111 and the holding device 141. In response, the constraining bar 130 can trigger, i.e., the trigger mechanism 140 can de-couple the constraining bar 130 from the housing 110. Particularly, once the proximal movement of the constraining bar 130 releases the holding device 141 from tension, the holding device elastic member 142 can pull the holding device 141 away from the holding device receiving member 144 into the retracted position. At this time, the constraining bar 130 can be released from tension (released position), and is capable of translating distally along the length of the receiving chamber RC.

At FIG. 4, v., as the constraining bar 130 is no longer held by the holding device 141, the one or more constraining bar elastic members 143 can pull the constraining bar 130 toward the distal end of the receiving chamber RC, such that the constraining bar 130 translates distally along the length of the receiving chamber RC. Distal translation of the constraining bar 130 causes corresponding distal translation of the object OBJ, as the constraining bar 130 pushes the object OBJ in the distal direction toward the proximal surface of the first and second paddles 120. Similarly, the affixed location 162 of the first and second locking ties 160 can translate distally along the length of the receiving chamber RC contemporaneously with the constraining bar 130. That is, the first and second locking ties 160 at the location 162 affixed to the constraining bar 130 (e.g., female zip-tie mechanisms) can move distally up the locking mechanism to the distal affixed location 161.

At FIG. 4, vi., the continued retraction of the one or more constraining bar elastic members 143 can push constraining bar 130 and the object OBJ in contact therewith distally until the object OBJ strikes the proximal (inner) surface of the first and second paddles. Here, the locking mechanism can prevent the constraining bar 130 from moving proximally, while the first and second constraining cords 150 can prevent the first and second paddles 120, respectively, from rotating outwardly (away from the receiving chamber RC). As a result, the object OBJ can be trapped securely inside of the constraining device 100 within the receiving chamber RC.

Referring next to FIGS. 5A-5D, a projecting shaft 200 can be coupled to the constraining device 100 and extend outwardly therefrom to provide distal projection of the constraining device 100 upon activation of an adjustable locking latch 230. As shown in FIGS. 5A-5D, which include operational cross-sectional views of a projecting shaft 200 coupled to the constraining device 100, the projecting shaft 200 can include an inner shaft 210 attached to the housing 110. In one example, the inner shaft 210 can be attached to the base portion 111 of the housing 110. The inner shaft 210 can be circularly shaped, although the shape thereof is not limited solely thereto.

The projecting device 200 can further include a hollow outer shaft 220 with a spring 221 disposed therein. The outer shaft 220 can be formed concentrically with the inner shaft 210, that is, formed to have the same shape as the inner shaft 210, with a larger diameter than that of the inner shaft 210 so as to receive the inner shaft 210 therein. As shown in FIGS. 5A-5D, the spring 221 can be disposed at a proximal end of the interior of the outer shaft 220. Thus, when the outer shaft 220 receives the inner shaft 210, a surface of the inner shaft 210 that is disposed inside of the outer shaft 220 can compress the spring 221 as the inner shaft 210 moves proximally against the spring 221.

The projecting device 200 can further include an adjustable locking latch 230 disposed on a surface of the outer shaft 220. The locking latch 230 can include a lever rotatably coupled to a pin (or similar device) configured to rotate about the pin between the locked and unlocked positions. A small protruding shaft (or similar device) can be disposed at one end of the lever. Furthermore, in some embodiments, an opening can be formed in both of the inner and outer shafts 210, 220 corresponding to the shape of the protruding shaft, such that the shaft can be inserted into said openings.

The locking latch 230 can be adjusted by a user of the constraining device 100 so as to transition between a "locked position" (e.g., see FIG. 5C), in which the locking latch 230 contacts the inner shaft 210 so as to lock together the inner shaft 210 and the outer shaft 220, and an "unlocked position" (e.g., see FIG. 5D), in which the locking latch 230 is removed from the inner shaft 210 so as to enable the inner shaft 210 to move independently of the outer shaft 220. In the locked position, the protruding shaft of the latch 230 can be inserted into the respective openings formed in the outer shaft 220 and the inner shaft 210, thus preventing the inner shaft 210 from moving independently of the outer shaft 220. Conversely, in the unlocked position, the protruding shaft can be removed from the opening of the inner shaft 210 (and, optionally, the opening of the outer shaft 220), thus de-coupling the inner shaft 210 from the outer shaft 220.

Figure 5A:
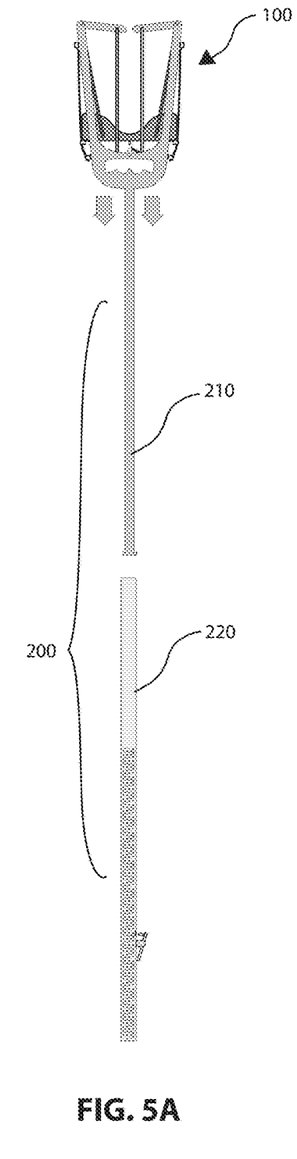
FIGS. 5A-5D include operational views of a projecting shaft coupled to the constraining device of FIGS. 1A-1C.
Figure 5B:
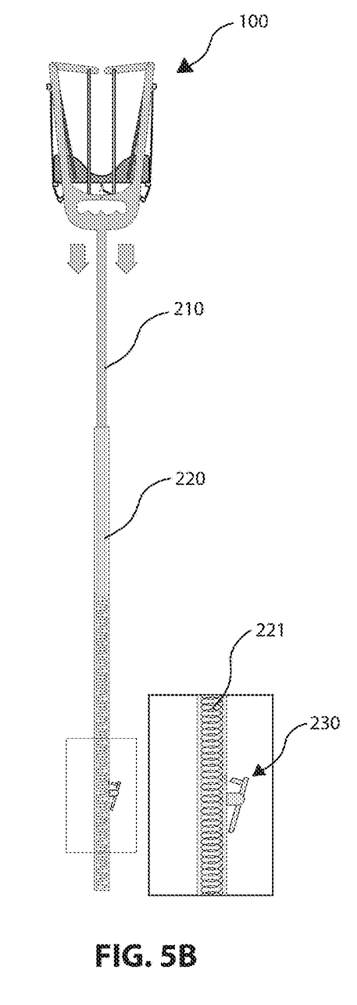

In operation, at FIGS. 5A and 5B, the inner shaft 210 which is attached to a proximal (bottom) portion of the housing 110, e.g., base portion 111, can be inserted proximally into a distal opening of the hollow outer shaft 220. A spring 221 can be disposed inside the outer shaft 220 at a proximal end thereof.

Figure 5C:
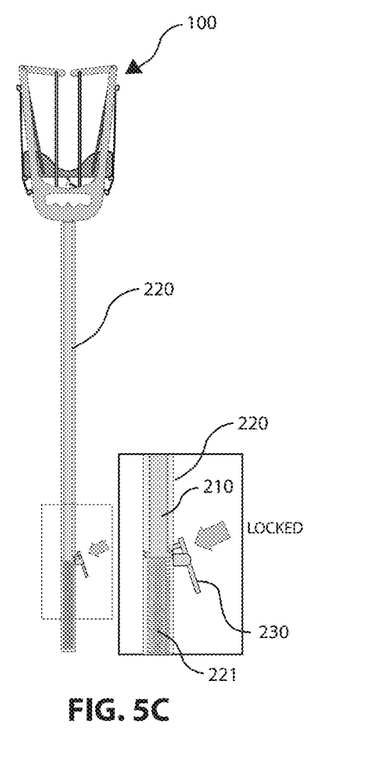

At FIG. 5C, as the inner shaft 210 is pushed further into the outer shaft 220, a proximal surface of the inner shaft 210 can come into contact with a distal surface of the spring 221. The proximal translation of the inner shaft 210 can, therefore, cause the spring 221 to compress, thus storing potential energy therein. The inner shaft 210 can travel proximally inside of the outer shaft 220 until the respective openings formed in the inner shaft 210 and outer shaft 220 overlap, such that the shaft of the locking latch 230 can penetrate the openings and lock the inner and outer shafts together, whereby the locking latch is in the locked position, as shown in FIG. 5C.

Figure 5D:
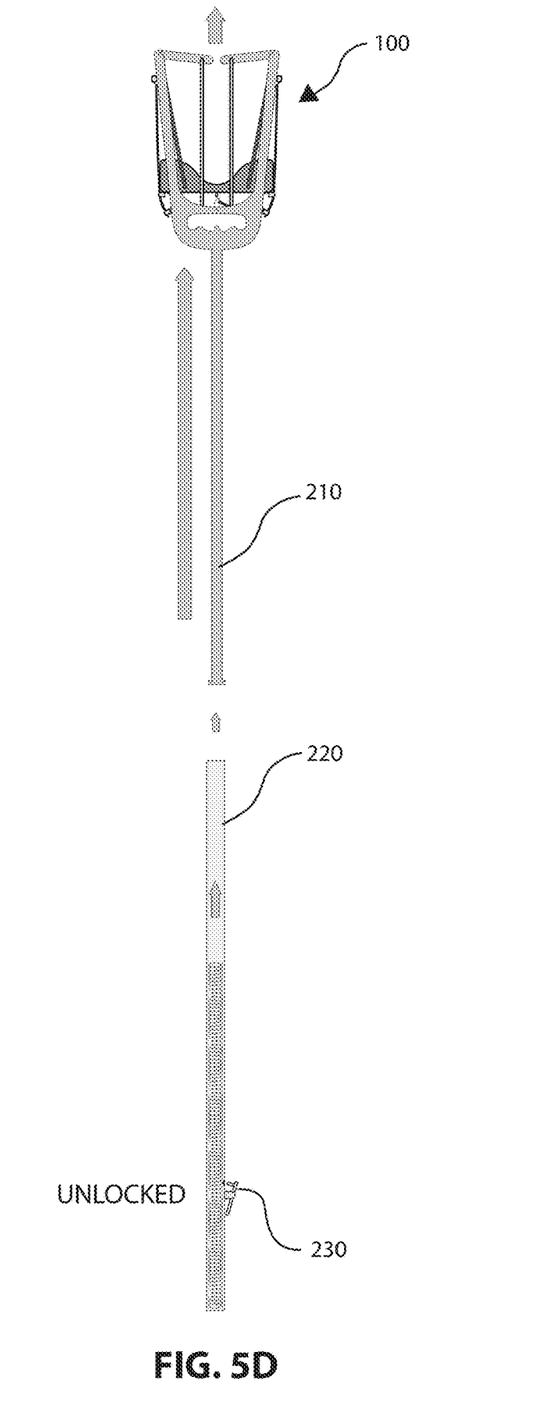

At FIG. 5D, the locking latch 230 can transition from the locked position to the unlocked position, e.g., by a user of the constraining device 100 pressing on the end of the lever opposite the protruding shaft so as to release the shaft from the opening formed in the inner shaft 210, thereby de-coupling the inner shaft 210 from the outer shaft 220. In response, the inner shaft 210 can accelerate in the distal direction as the spring 221 disposed inside of the outer shaft 220 decompresses. This can cause longitudinal movement of the inner shaft 210 in the distal direction independent of the outer shaft 220. Because the inner shaft 210 is attached to the housing 110 of the constraining device 100, the constraining device 100 can also accelerate in the distal direction. Such a configuration can be advantageous if the user wishes to launch the constraining device 100 toward a target, for example.

Accordingly, the constraining device described herein provides users with a mechanism for quickly and securely surrounding and constraining a target. The constraining device can be deployed in a non-lethal manner, allowing the user to effectively constrain a target without causing serious injury.

The foregoing description has been directed to certain embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. An apparatus configured to constrain an object therein while operating in a constraining state, the apparatus comprising:
   a housing configured to form a receiving chamber that is operable to receive the object, the housing having a base portion disposed at a proximal end of the housing and first and second housing arms extending outwardly from the base portion to form an opening at a distal end of the housing, the first and second housing arms disposed at opposite sides of the receiving chamber, respectively;
   first and second paddles disposed at a distal end of the receiving chamber, the first and second paddles rotatably coupled to respective distal ends of the first and second housing arms and extending inwardly therefrom;
   a constraining bar movably disposed within the housing and configured to translate linearly along a length of the receiving chamber, the constraining bar configured to move between a loaded position in which the constraining bar is positioned at a proximal end of the receiving chamber under tension and a released position in which the constraining bar is released from tension and positioned distal of the proximal end of the receiving chamber; and
   a trigger mechanism configured to releasably couple the constraining bar to the base portion,
   wherein, when the constraining bar is in the loaded position, the trigger mechanism is configured to release the constraining bar in response to a proximally-directed force directed toward the proximal end of the housing exerted on the constraining bar, causing the constraining bar to translate distally toward the distal end of the housing along the length of the receiving chamber, resulting in the constraining state of the apparatus.

2. The apparatus of claim 1, wherein the trigger mechanism is configured to couple the constraining bar to the base portion when the constraining bar is in the loaded position and to de-couple the constraining bar from the base portion when the constraining bar is in the released position.

3. The apparatus of claim 1, wherein the trigger mechanism includes a holding device rotatably disposed on the base portion, the holding device configured to rotate between a holding position in which the holding device attaches to the constraining bar when the constraining bar is in the loaded position, such that the constraining bar is prevented from translating distally along the length of the receiving chamber, and a retracted position in which the holding device detaches from the constraining bar when the constraining bar is in the released position, such that the constraining bar is enabled to translate distally along the length of the receiving chamber.

4. The apparatus of claim 3, wherein the holding device is configured to extend in a direction parallel to the length of the receiving chamber when the holding device is in the holding position and to extend in a direction non-parallel to the length of the receiving chamber when the holding device is in the retracted position.

5. The apparatus of claim 3, wherein the trigger mechanism further includes a holding device elastic member connected at a first end thereof to the base portion and at a second end thereof to the holding device, the holding device elastic member configured to transition between a resting state when the holding device is in the retracted position and a tensioned state when the holding device is in the holding state, causing extension of the holding device elastic member.

6. The apparatus of claim 5, wherein the trigger mechanism further includes one or more constraining bar elastic members connected at a first end thereof to the constraining bar and at a second end thereof to a distal portion of the housing, the one or more constraining bar elastic members configured to transition between a resting state when the constraining bar is in the released position and a tensioned state when the constraining bar is in the loaded position, causing extension of the one or more constraining bar elastic members.

7. The apparatus of claim 6, wherein, when the holding device is in the holding position, causing the one or more constraining bar elastic members to be in the tensioned state, the holding device and the one or more constraining bar elastic members are configured to exert opposing forces on the constraining bar, such that the constraining bar is held in the loaded position under tension.

8. The apparatus of claim 6, wherein, in response to the proximally-directed force exerted on the constraining bar when the constraining bar is in the loaded position, causing temporary proximal translation of the constraining bar, the holding device elastic member is configured to pull the holding device toward the retracted position, such that the constraining bar is released from tension, and the one or more constraining bar elastic members are configured to pull the constraining bar toward the distal end of the receiving chamber, such that the constraining bar translates distally along the length of the receiving chamber.

9. The apparatus of claim 1, wherein the first and second paddles are rotatably coupled to the respective distal ends of the first and second housing arm via first and second axle members mounted to the housing, such that the first and second paddles are configured to rotate about the first and second axle members, respectively.

10. The apparatus of claim 1, wherein the first and second paddles are configured to rotate between a neutral position in which the first and second paddles are held at rest and an inwardly rotated position in which the first and second paddles rotate inwardly with respect to the receiving chamber from the neutral position.

11. The apparatus of claim 10, wherein, when the first and second paddles are in the neutral position, the first and second paddles extend inwardly from the respective distal ends of the first and second housing arms at an angle substantially perpendicular to the first and second housing arms.

12. The apparatus of claim 10, further comprising first and second paddle elastic members connected at a first end thereof to the first and second paddles, respectively, and at a second end thereof to the housing, the first and second paddle elastic members configured to transition between a resting state when the first and second paddles are in the neutral position and a tensioned state when the first and second paddles are in the inwardly rotated position, causing extension of the first and second paddle elastic members.

13. The apparatus of claim 12, wherein, when the first and second paddles are in the inwardly rotated position, the first and second paddle elastic members are configured to pull the first and second paddles, respectively, in a direction causing the first and second paddles to rotate outwardly with respect to the receiving chamber toward the neutral position.

14. The apparatus of claim 10, further comprising first and second constraining cords connected at a first end thereof to the first and second paddles, respectively, and at a second end thereof to the base portion, the first and second constraining cords configured to prevent the first and second paddles from rotating outwardly with respect to the receiving chamber from the neutral position.

15. The apparatus of claim 1, further comprising a locking mechanism coupled to the housing and the constraining bar, wherein the locking mechanism is configured to prevent the constraining bar from translating proximally along the length of the receiving chamber when the constraining bar is released from the loaded position.

16. The apparatus of claim 15, wherein the locking mechanism includes first and second locking ties extending at least partially along the length of the receiving chamber and coupled to the housing and the constraining bar, the first and second locking ties configured to enable the constraining bar to translate distally along the length of the receiving chamber while preventing the constraining bar from translating proximally along the length of the receiving chamber.

17. The apparatus of claim 16, wherein the first and second locking ties are coupled to the housing at a plurality of locations, including a distal location of the housing and a proximal location of the housing, and movably coupled to the constraining bar at a location between the distal location of the housing and the proximal location of the housing.

18. The apparatus of claim 1, wherein the housing includes first and second housing plates connected to each other via a plurality of connecting rods extending in a direction perpendicular to the length of the receiving chamber, forming a gap between the first and second housing plate.

19. The apparatus of claim 18, wherein at least a portion of the constraining bar is disposed in the gap between the first and second housing plates, and at least a portion of the first and second paddles is disposed in the gap between the first and second housing plates.

20. The apparatus of claim 1, further comprising a projecting shaft coupled to the base portion and extending outwardly therefrom, the projecting shaft including:
   an inner shaft attached to the housing;
   a hollow outer shaft with a spring disposed therein, the outer shaft configured to receive the inner shaft; and
   an adjustable locking latch disposed on a surface of the outer shaft, the locking latch configured to transition between a locked position in which the locking latch contacts the inner shaft so as to lock together the inner shaft and the outer shaft and an unlocked position in which the locking latch is removed from the inner shaft so as to enable the inner shaft to move independently of the outer shaft,
   wherein, when the outer shaft receives the inner shaft, such that a surface of the inner shaft that is disposed inside of the outer shaft compresses the spring, the spring is configured to decompress when the locking latch is transitioned from the locked position to the unlocked position, causing longitudinal movement of the inner shaft independent of the outer shaft.

* * * * *